US011802987B2

(12) United States Patent
Guy

(10) Patent No.: US 11,802,987 B2
(45) Date of Patent: Oct. 31, 2023

(54) SYSTEM AND METHOD FOR DETERMINING INFRASTRUCTURE RISK ZONES

(71) Applicant: Utilis Israel Ltd., Kfar-Saba (IL)

(72) Inventor: Lauren Guy, Beer Sheva (IL)

(73) Assignee: Utilis Israel Ltd., Kfar-Saba (IL)

( * ) Notice: Subject to any disclaimer, the term of this patent is extended or adjusted under 35 U.S.C. 154(b) by 73 days.

(21) Appl. No.: 17/467,219

(22) Filed: Sep. 5, 2021

(65) Prior Publication Data

US 2022/0075089 A1  Mar. 10, 2022

(30) Foreign Application Priority Data

Sep. 9, 2020  (GB) .................................... 2014152

(51) Int. Cl.
*G01V 3/12* (2006.01)
*G01N 21/25* (2006.01)
*G01N 33/24* (2006.01)

(52) U.S. Cl.
CPC ............... *G01V 3/12* (2013.01); *G01N 21/25* (2013.01); *G01N 33/246* (2013.01)

(58) Field of Classification Search
CPC . G01V 3/12; G01V 3/16; G01N 21/25; G01N 33/246; G01S 7/025; G01S 13/885; G01S 13/9027; G01S 13/9076
See application file for complete search history.

(56) References Cited

U.S. PATENT DOCUMENTS 9,285,475 B1 * 3/2016 Guy ..................... G01V 3/12
9,945,942 B2 * 4/2018 Guy ..................... G01S 7/411

(Continued)

FOREIGN PATENT DOCUMENTS

CN  112014542 A  12/2020
EP  3367083 A1  8/2018

(Continued)

OTHER PUBLICATIONS

Ciampalini, A. et al. (2015). Improved estimation of soil clay content by the fusion of remote hyperspectral and proximal geophysical sensing. Journal of Applied Geophysics. 116. 135-145. 10.1016/j.jappgeo.2015.03.009.

(Continued)

*Primary Examiner* — Alexander Satanovsky
*Assistant Examiner* — Asm Fakhruddin
(74) *Attorney, Agent, or Firm* — The Roy Gross Law Firm, LLC; Roy Gross

(57) ABSTRACT

A system and a method for determining infrastructure risk zones is disclosed. The system and method may include: receiving, from a radiofrequency (RF) radiation sensor, a first scan of an area, wherein the area at least partially comprises the infrastructure; receiving additional data; filtering electromagnetic noise from the first scan using the additional data; receiving infrastructure location in the area; determining an examination zone around the infrastructure; estimating the amount of clay in soil included in the examination zone, from the filtered scan; calculating soil moisture content at locations in the examination zone, from the filtered scan; and determining location at risk having soil moisture content above a predetermined threshold, wherein the threshold may be determined based on the estimated clay amount.

13 Claims, 15 Drawing Sheets

(56) References Cited

U.S. PATENT DOCUMENTS

| | | | |
|---|---|---|---|
| 2008/0262988 A1* | 10/2008 | Williams | G06N 3/126 |
| | | | 405/36 |
| 2015/0096368 A1* | 4/2015 | O'Brien | E02D 1/00 |
| | | | 73/32 R |
| 2018/0106899 A1 | 4/2018 | Guy | |
| 2018/0224550 A1 | 8/2018 | Guy | |
| 2019/0025423 A1 | 1/2019 | Sajwaj et al. | |

FOREIGN PATENT DOCUMENTS

| | | | | |
|---|---|---|---|---|
| ES | 2577403 B2 * | 7/2016 | | F41H 11/13 |
| RU | 2467314 C1 * | 11/2012 | | |
| WO | 2001004627 A1 | 1/2001 | | |
| WO | 2016151579 A2 | 9/2016 | | |

OTHER PUBLICATIONS

Misilimba, G.G., Holmes, P.J. A Landslide Hazard Assessment and Vulnerability Appraisal Procedure: Vunguvungu/Banga Catchment, Northern Malawi. Nat Hazards 34, 199-216 (2005). https://doi.org/10.1007/s11069-004-1513-2.

M. Nolan and D. R. Fatland, "Penetration depth as a DInSAR observable and proxy for soil moisture," in IEEE Transactions on Geoscience and Remote Sensing, vol. 41, No. 3, pp. 532-537, Mar. 2003, doi: 10.1109/TGRS.2003.809931.

Hill, C., Verjee, F., & Barrett, C. (2010) Flash Flood Early Warning System Refrence Guide. University Corporation for Atmospheric Research (UCAR) Comet program and National Oceanic and Atmospheric Administration (NOAA).

* cited by examiner

SYSTEM AND METHOD FOR DETERMINING INFRASTRUCTURE RISK ZONES

CROSS REFERENCE TO RELATED APPLICATIONS

This application claims the benefit of priority of Great Britain Patent Application No. 2014152.9 having filing date of Sep. 9, 2020, the contents of which is all incorporated herein by reference in their entirety.

FIELD OF THE INVENTION

The present invention relates generally to remote detection of infrastructure risk zones. More specifically, the present invention relates to systems and methods for remote detection of infrastructure risk zones due to soil moisture, using microwave radiation.

BACKGROUND OF THE INVENTION

Water, and more specifically, hidden water is the enemy of infrastructure. Water plays a key role in the mechanical performance and lifetime of any infrastructure. For example, if there is no excess water in road structures and in the subgrade soil, the road will perform well. Increased water content reduces the bearing capacity of the soil or aggregate, which under traffic loading will increase the rate of deterioration, increase the risk of road collapse, and shorten the lifetime of the road. In such cases, the road will need maintenance measures and rehabilitation more often than a well-drained road structure. For this reason, road drainage systems need to work effectively over the lifetime of the pavement. Current predictions of the likely effects of climate change only magnify this issue and modern asset management principles are rightly forcing road owners to consider ways to maximize the use of their available budgets and improve road lifetimes.

However, monitoring the water content is a huge challenge in pavement structures and subgrade soils. Another challenge is monitoring the effectiveness of the drainage system in draining the structures sufficiently to ensure adequate bearing capacity in the road infrastructure.

In mountainous areas additional factors are added to the risk of land collapse or landslide. All studies and research on landslides triggering mechanisms point to the initial water content as the prime factor. In mountainous terrain, rainfall-induced landslides pose a serious risk to people and infrastructure. For rainfall-triggered landslides, the availability of unconsolidated material, the topography, the vegetation cover, and the hydrological preconditions (pre-wetting of the hillslope) determine the susceptibility of a slope to slide and are referred to as "cause factors".

While rainfall measurements are available in increasing spatial resolution and awareness, and being used in different models, using rainfall thresholds and rainfall-based indices for landslide early warning and as a result damage to the infrastructure is very limited and in most cases is not with correlation with infrastructure risk zones.

There is no good current solution for comprehensive detection of potential collapses in infrastructure and land. Most solutions are focused on the micro level, using sensors, core samples and other geomorphological means.

SUMMARY OF THE INVENTION

Embodiments of the invention are directed to a system and a method for determining infrastructure risk zones. The embodiments may include: receiving, from a radiofrequency (RF) radiation sensor, a first scan of an area at a first polarization, the first scan including first radiofrequency reflections from the area at a first resolution, the sensor being located at least 50 meters above the area, wherein the area at least partially comprises the infrastructure; receiving additional data; filtering electromagnetic noise from the first scan using the additional data; receiving infrastructure location in the area; determining an examination zone around the infrastructure; estimating the amount of clay in soil included in the examination zone, from the filtered scan; calculating soil moisture content at locations in the examination zone, from the filtered scan; and determining location at risk having soil moisture content above a predetermined threshold. In some embodiments, the threshold is determined based on the estimated clay amount.

In some embodiments, topographical data of the area may be received and drainage divide surrounding at least part of the infrastructure, may be identified. In some embodiments, the examination zone may be the drainage divide.

Embodiments of the invention are directed to a system and a method of determining underground liquid (e.g., water) content. Embodiments may include: receiving a first scan of an area at a first polarization, the first scan including first RF reflections (e.g., L band microwave reflections) from the area, receiving a second scan of the area at a second polarization, the second scan including second RF reflections (e.g., L band microwave reflections) from the area, the first and second scans being from a first sensor for RF radiation reflections attached to an object located at least 50 meters ("m"), 70 m, 100 m or more, above the area and filtering electromagnetic noise from the first scan using the second scan. Embodiments of the method may include creating a water composition map based on typical salinity values (e.g., a water roughness map based on typical roughness values) of various types of water sources and the filtered first scan, identifying a first type of water sources using the water composition map and the filtered first scan and calculating the water content at locations in the area based on the identified first type of water sources.

Embodiments of the invention include a method of determining underground liquid (e.g., water) content. Embodiments of the method may include: receiving a first scan of an area at a first polarization, the first scan including first RF reflections (e.g., L band microwave reflections from the area), the first scan being from a first sensor for detecting RF radiation reflections, the first sensor attached to an object located at least 50 meters ("m"), 70 m, 100 m or more, above the area. Embodiments of the method may further include receiving optical data of or representing at least a portion of the scanned area. According to some embodiments, the optical data may be captured in a wavelength in a range between 1 millimeter to 10 nanometers (e.g., from infrared to ultraviolet). According to some embodiments of the method electromagnetic noise from the first scan may be filtered using the optical data. Embodiments of the method may include creating a water composition map based on typical salinity values of various types of water sources and the filtered first scan, identifying a first type of water sources using the water composition map and the filtered first scan and calculating the water content at locations in the area based on the identified first type of water sources.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
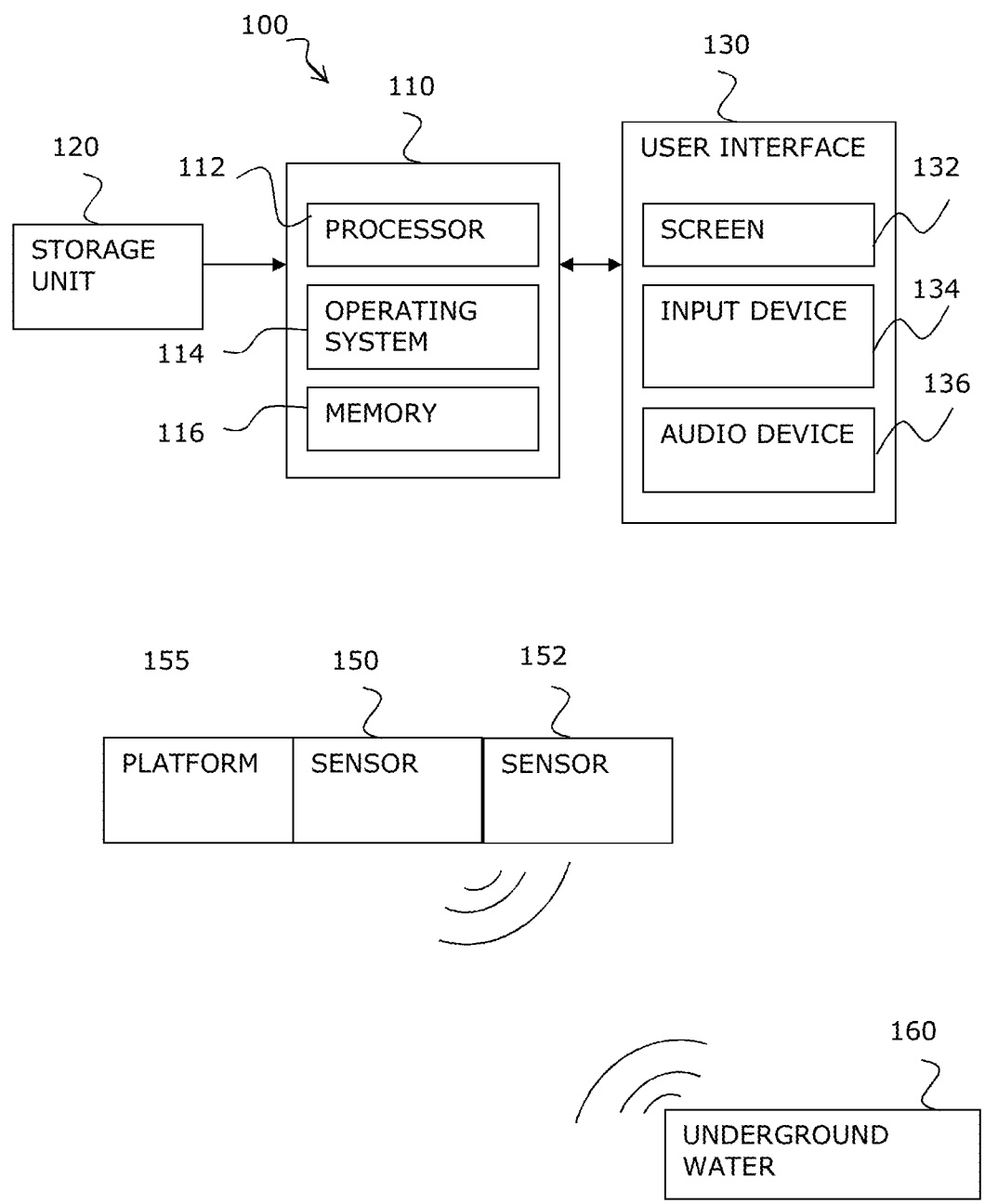
FIG. 1 is high level block diagram of a system for detecting underground water according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory processor-readable storage medium that may store instructions, which when executed by the processor, cause the processor to perform operations and/or processes as discussed herein. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof may occur or be performed simultaneously, at the same point in time, or concurrently.

Embodiments of the invention are related to a method and a system for remote detection of underground water, for example, drinking water leakage from an urban water system. Water sources such as water pipes, lakes, swimming pools or the like reflect electromagnetic (EM) waves, both underground and above ground level.

Water may reflect back EM waves at frequencies in the RF range, for example, microwaves in L band frequencies, P band frequencies, C band frequencies and the like. As used herein frequencies in the RF range may include any of the EM wave frequencies that are in the range from 20 KHz to 300 GHz.

Every water source has typical reflections and typical EM behavior, the type of the water source may be identified using these typical reflections. EM sensors placed on an elevated platform for example, a satellite, an aircraft, an air balloon or the like, may send EM waves at a known frequency (e.g., 1.3 GHz) towards an area and read the EM waves reflected back from that area. The sensor may send a scan that includes all the reflections detected from a particular area to further be processed by a system according to some embodiments of the invention. The sensor may include Synthetic-Aperture Radar (SAR) SAR which uses a motion of a SAR antenna over a target region to provide finer spatial resolution than is possible with conventional beam-scanning radars. The scan may include all the EM reflections received from the area. These reflections may include both reflections from water sources and undesired reflections from other bodies in the area, such as buildings, vegetation and other topographical feature of the area. In order to identify the water related reflections, the undesired reflections (e.g., EM noise reflection) may be filtered or removed from the scan. In order to reduce (e.g., remove or filter) the EM noise two or more scans may be taken from the area at two different polarizations, for example, a horizontal-vertical (HV) scan and horizontal-horizontal (HH) scan. The HH reflections may be received from transmitting waves having a horizontal polarization that were received at horizontal modulation. The HV reflections may be received from transmitting waves having a horizontal polarization that were received at vertical modulation.

Some embodiments of the invention may transmit and receive reflections having two different resolutions. For example, HH and HV scans may be received from a first sensor having a first resolution and an additional HH (and/or HV) scan may be received from a second sensor, such that the second sensor has a higher resolution (e.g., 6 m$^3$) than the resolution of the first sensor (e.g., 12 m$^3$). The scans from the first sensor may be used to identify the EM noise reflections and to filter them from (e.g., remove them from) the scan received from the second sensor. In some embodiments, all the scans may be received from a single sensor having a high resolution (e.g., 6 m$^3$, 3 m$^3$). Two HH and HV scans may be received from a single sensor and may include all the information required for filtering (e.g., reducing) the EM noise and receiving a scan having a sufficient resolution. In some embodiments, additional scans having additional polarizations may be received from the single sensor all in the same resolution. Such additional scans may allow further reduction of the EM noise.

After the filtration of the EM noise at least some of the scanned reflections may be identified as water reflections. Since different water sources (e.g., drinking water, sewage, seas, lakes swimming pools, etc.) have different typical EM roughness (typical EM reflections) due to different salinity levels, it may be possible to distinguish one from the other. In some embodiments, EM reflections from sewage pipes, seas, lakes and swimming pools may be filtered or removed from the filtered noise scan thus leaving in the scan only reflection received from water leakages. Since the resolution (e.g., at least 3 m$^3$) of the scan is larger than the diameter of the pipes only a leakage larger than this resolution may be detected and not the pipes themselves.

In some embodiments, a drinking water content or amount may be calculated from the drinking water related reflections and converted into quantities of water capacity (e.g., cubic meters/hour, gallons/hour, etc.). This information may be displayed on a geographical map (e.g., a street map of a city) showing, for example, the amount and location of each suspected leakage in a city.

In some embodiment, the received scans may be used for determining infrastructure risk zones, which include locations having higher risk for collapsing due to on ground and/or underground water and/or areas that are more likely to be affected by landslides or soil movements due to one or more of soil water content, topography of the area, soil parameters, and the like. As used herein, the term infrastructure refers to a man-made construction and may include facilities and systems serving a country, city, or other area. For example, infrastructure may include, roads, railways, bridges, tunnels, water supply systems, sewer systems, electrical grids, buildings, power plants, parking lots, industrial areas and the like. Thus, in embodiments, the invention is directed to identifying zones where such infrastructure installations may be at risk for lack of support.

In some embodiments, an examination zone, at which infrastructure risk zones may be identified, may be determined. The examination zone may be determined to encompass the infrastructure, included in the scanned area, or a portion thereof. The examination zone may be predetermined at a fixed distance surrounding the infrastructure (e.g., 20 meters from each side of a road, a railway, a bridge and the like) or may be determined based on the topography (e.g., based on a drainage divide) or other data, such as the amount of clay in the soil.

The received RF reflection scan(s) may be used for determining an amount of clay in the soil located in the examination zone. The amount of clay may affect the ability of the soil to absorb water. In some embodiments, soil moisture content at various locations in the examination zone may further be calculated. In some embodiments, an infrastructure risk zone may be determined as a location having soil moisture above a threshold value. The threshold value may be set based on the calculated amount of clay.

Reference is now made to FIG. 1 which is high level block diagram of an exemplary system for remote detecting underground water according to some embodiments of the invention. A system 100 may include a computer processing device 110, a storage unit 120 and a user interface 130. System 100 may receive from a sensor 150 L band microwave scans from an area that includes at least one underground water source 160. Processing unit 110 may include a processor 112 that may be, for example, a central processing unit (CPU), a chip or any suitable computing or computational device, an operating system 114 and a memory 116. System 100 may be included in a desktop computer, laptop commuter, a tablet, a mainframe computer or the like. Processor 112 or other processors may be configured to carry out methods according to embodiments of the present invention by for example executing instructions stored in a memory such as memory 116. In some embodiments, system 100 may further receive form a second sensor 152 L band microwave scans from an area that includes at least one underground water source 160.

Operating system 114 may be or may include any code segment designed and/or configured to perform tasks involving coordination, scheduling, arbitration, supervising, controlling or otherwise managing operation of processing device 110, for example, scheduling execution of programs. Operating system 114 may be a commercial operating system. Memory 116 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 116 may be or may include a plurality of, possibly different memory units.

Memory 116 may store any executable code, e.g., an application, a program, a process, operations, task or script. The executable code may when executed by a processor cause the processor to detect underground water and perform methods according to embodiments of the present invention. The executable code may be executed by processor 112 possibly under control of operating system 114. Memory 116 may store data such as for example images, gray scale or intensity levels, scans, reflections, etc.

Storage 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Content may be stored in storage 120 and may be loaded from storage 120 into memory 116 where it may be processed by processor 112. For example, storage 120 may include scans of L band microwaves of areas at various polarizations received from sensor 150, geographical data related to the scanned area (e.g., a type of soil, amount of humidity in the solid, a road map, etc.), and salinity values of various types of water sources or any other required data according to embodiments of the invention.

User interface 130 may be, be displayed on, or may include a screen 132 (e.g., a monitor, a display, a CRT, etc.), an input device 134 and an audio device 136. Input device 134 may be a keyboard, a mouse, a touch screen or a pad or any other suitable device that allows a user to communicate with processor 112. Screen 132 may be any screen suitable for displaying maps and/or scans according to embodiments of the invention. In some embodiments, screen 132 and input device 134 may be included in a single device, for example, a touch screen. It will be recognized that any suitable number of input devices may be included in user interface 130. User interface 130 may include audio device 136 such as one or more speakers, earphones and/or any other suitable audio devices. It will be recognized that any suitable number of output devices may be included in user interface 130. Any applicable input/output (I/O) devices may be connected to processing unit 110. For example, a wired or wireless network interface card (NIC), a modem, printer or facsimile machine, a universal serial bus (USB) device or external hard drive may be included in user interface 130.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

The storage medium may include, but is not limited to, any type of disk including floppy disks, optical disks, compact disk read-only memories (CD-ROMs), rewritable compact disk (CD-RWs), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage unit.

A system 100 may include or may be, for example, a personal computer, a desktop computer, a mobile computer, a laptop computer, a notebook computer, a terminal, a workstation, a server computer, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Sensor 150 and/or sensor 152 may be any sensor that is configured to scan and detect underground water, such as underground water source 160 using electromagnetic radiation. For example, sensor 150 may include a receiver for a radar or Synthetic-Aperture radar (SAR) SAR. Sensors 150 and/or 152 may be placed for example on an elevated platform or structure 155. Elevated platform or structure 155, may be for example, a satellite, an aircraft or an air balloon and may be located at least 50 meters above the ground (e.g., at an elevation of 50 m), for example, 70 meters, 100 meters, 150 meters, 500 meters, 1000 meters or more. Sensor 152 may have different detection resolution (e.g., higher resolution) than sensor 150.

Figure 2:
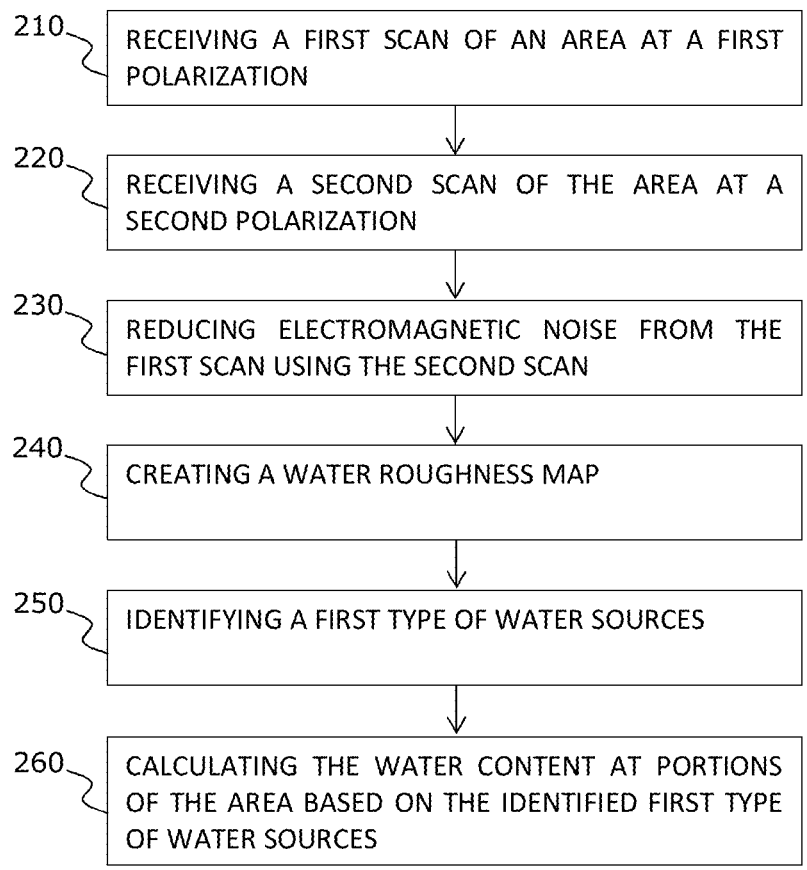
FIG. 2 is a flowchart of a method of detecting underground water according to some embodiments of the invention.

Reference is made to FIG. 2, a flowchart of an exemplary method of remote detecting underground water according to some embodiments of the invention. Embodiments of the method of FIG. 2 may be performed for example by system 100 or by another system. In operation 210, embodiments of the method may include receiving a first scan of an area at a first polarization. The first scan may be a two-dimensional scan of an area. The first scan may include a first L band microwave reflections from the area. The first scan may include reflections received from a predefined area on the ground, converted into data, e.g., data including pixel data. The size of each pixel may depend on the resolution of a sensor (e.g., sensor 150, 152) located at least 50 meters above the ground. The sensor may receive reflection from both above ground and underground objects. A processor associated with the sensor may convert these reflections into data including pixels having different gray-levels. This data may be received and analyzed by system 100. The size of the area scanned is determined by the sensor (e.g., a SAR sensor) and may be received as raw data. The gray scale level of each pixel converted from microwave reflection of the scan may be related to a reflection intensity level received from a single area unit (e.g., 3 m$^2$) at a respective depth (e.g., 3 m). For example, a pixel may be related to reflections received from 2 m$^3$, 3 m$^3$, 6 m$^3$, 12 m$^3$, or the like.

L band microwave reflections or other radiofrequency (RF) wave reflections may be received from a sensor for detecting L band microwave or RF radiation reflections (e.g., sensor 150 or 152). The sensor may be attached to an object (e.g., platform 155) located at least 50, 100 meters, 1000 meters or more above the area. Such a sensor may be attached to an elevated platform, for example, a satellite, an aircraft or an air-balloon. L band microwaves (e.g., radiofrequency waves in a frequency range of 1-2 GHz) or other RF waves may be transmitted from a transmitter towards the scanned area and reflected back from the scanned area after interacting with object both above the ground and under the ground. The penetration depth of L band microwaves into the ground may vary with the type of the soil, the amount of moisture in the soil, the structure of the land cover or the like. Exemplary penetration depth may be between soil surface to 3 meters depth from a remote object located at least 50 meters above soil surface. L band microwaves reflected back from the scanned area may be received and detected by the sensor. The sensor may identify reflections having different polarizations. Sensors 150 and 152 may each be configured to detect reflections having different resolution, for example, the sensors may be used for receiving scans at resolutions of 6 m$^3$ and 12 m$^3$.

The L band microwaves or other RF waves may be transmitted in a first polarization, for example, a horizontal polarization or a vertical polarization and the sensor may detect reflections having various modulations. For example, reflections from waves that were transmitted at horizontal polarization may be detected at vertical modulation (HV polarization) or may be detected at horizontal modulation (HH polarization). Other polarizations may include vertical-vertical (VV) polarization and vertical-horizontal (VH) polarization.

In operation 220, embodiments of the method may include receiving a second scan of the area at a second polarization. The second scan may include second L band microwave reflections from the same area. In some embodiments, if the first polarization is an HV polarization, than the second polarization may be HH polarization. In some embodiments, the second polarization may be VH polarization or VV polarization. Embodiments of the method may include receiving a third scan of the area at a second polarization (e.g., HH polarization), the third scan including third L band microwave reflections from the area at a higher resolution than that of the first and second scans. For example, if the first and second scans are received from a first sensor, at a resolution of 12 m$^3$, the third scan may be received, from a second sensor for detecting L band microwave radiation reflections, at a resolution of 6 m$^3$. The second sensor may be attached to an object (e.g., a satellite, an airplane or an air-bloom) located at least 50 meters, 100 meters, 1000 meters or more above the area, calibrated similarly to the first sensor, such that a gray level of a pixel converted from an intensity level of microwave reflections in the first and second scans received from a specific location in the area may have corresponding gray level of a pixel (or pixels) converted from an intensity level of microwave reflections in the third scan received from that specific location. For example, if the first and second scans have a resolution of 12 m$^3$ (or 13×6 m$^2$) for every pixel in the first and second scans 4 corresponding pixels (or 2 corresponding pixels) may be received in the third scan. Other numbers of scans may be used.

Figure 3A:
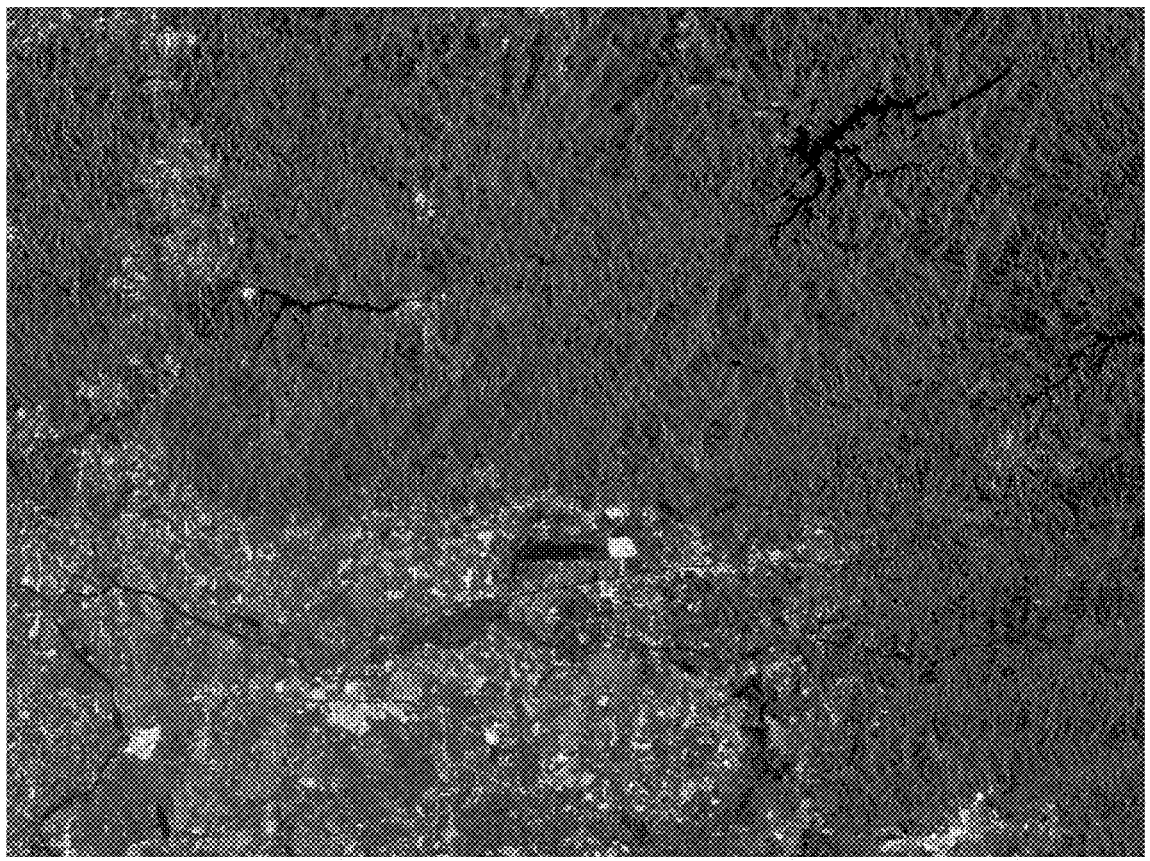
FIGS. 3A-3B are scans of L band microwave reflections from the area a horizontal-vertical (HV) and horizontal-horizontal (HH) polarizations according to some embodiments of the invention.
Figure 3B:
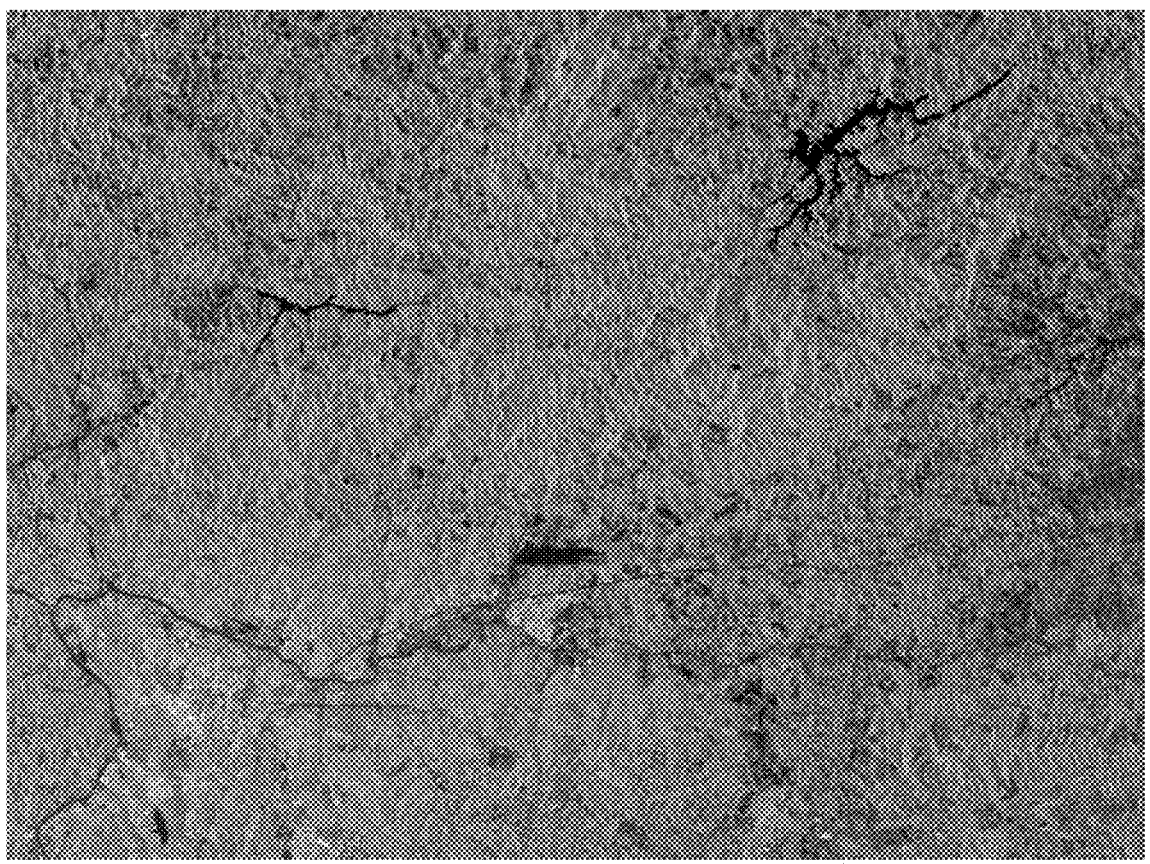

The first, second and optionally the third scans may be received as grayscale images of microwave intensity levels converted into grayscale levels (e.g. each pixel in the map has different gray level). Exemplary scans received at a resolution of 12 m$^3$ are given in FIGS. 3A and 3B. FIGS. 3A and 3B are exemplary scans taken above an urban area in Oakland, Calif., as received from an L-band microwave sensor (e.g., a SAR) located on a satellite. FIG. 3A is a scan having a HV polarization and FIG. 3B is a scan having a HH polarization. In some embodiments, the method may include converting the first and second L band microwave reflections from gray scale levels to intensity levels. As used herein gray scale levels may be defined according to the ratio between black pigment or level and white pigment or level at each pixel. The gray levels may be correlated to microwave reflection intensity. The higher the amount of black level or pigment the higher is the intensity of the microwave reflection from a particular area (e.g., pixel). For example, the gray scale level data received from the sensor may be converted to Decibel (dB) intensity level, using for example, equation 1:

$$I_{dB} = 10 \cdot \log(DN^2) - 83 \quad (1)$$

wherein, $I_{dB}$ is the converted intensity level in each pixel and DN is the gray scale level in each pixel.

It should be understood by those skilled in the art, that equation 1 is given as an example only and converting gray levels to other intensity levels using different equations are within the scope of the invention. Embodiments of the method may include converting also the third scan from gray scale into intensity levels.

Embodiments of the method may include receiving a fourth scan of the area at a third polarization, the fourth scan including fourth L band microwave reflections from the area. For example, the fourth scan may include reflections having VH polarization. Embodiments of the method may include receiving a fifth scan of the area at a forth polarization, the fifth scan including fifth L band microwave reflections from the area. For example, the fourth scan may include reflections having VV polarization. The fourth and fifth scans may be received from the first sensor (e.g., a sensor having a resolution of 6 m$^3$).

In some embodiments, all the received scans (e.g., first-fifth) may be converted from gray scale to intensity levels, using for example, equation (1).

In operation 230, embodiments of the method may include filtering electromagnetic (EM) noise from the first scan using the second scan. The electromagnetic noises may include reflections reflected or bounced from buildings, vegetation or other topographical features located at the scanned area. There are several methods known in the art for filtering EM noise from EM and RF signals and the invention is not limited to a particular method or algorithm. Some exemplary methods for filtering EM noise, from each pixel, according to embodiments of the invention may include reducing noise from buildings using for example the following equations (as with other equations discussed herein, other or different equations may be used):

$$Fd = \frac{1}{2}(HH_{dB}^2 - 2 \cdot HV_{dB}^2) \quad (2)$$

wherein Fd is electromagnetic noise from bouncing reflection from solid objects located in the scanned area, $HH_{dB}$ is the intensity level of HH polarization reflection at that pixel, and $HV_{dB}$ is the intensity level of HV polarization reflection at that pixel. In some embodiments, filtering electromagnetic noise may include filtering reflection received from solid objects located in the scanned area.

$$C = (HH_{dB}^2)/(2Fd) \quad (3)$$

$$Fv = 2 \cdot (\frac{1}{2}HH_{dB}^2 - Fd \cdot C^2) \quad (4)$$

wherein Fv is the calculated electromagnetic reflection noise received from solid objects located in the scanned area.

In some embodiments, reflections from additional polarizations (e.g., VV and VH polarizations) may be used to filter the EM noise. For example, such reflections may be included in an extended equation (2). Various parameters such as Fv and C calculated in equations (2)-(4) may be used to calculate a filtered first scan, according to equation (5).

$$Bs = HH_{dB} - (\text{the EM noise}) \quad (5)$$

wherein Bs is filtered EM noise refection

Figure 4:
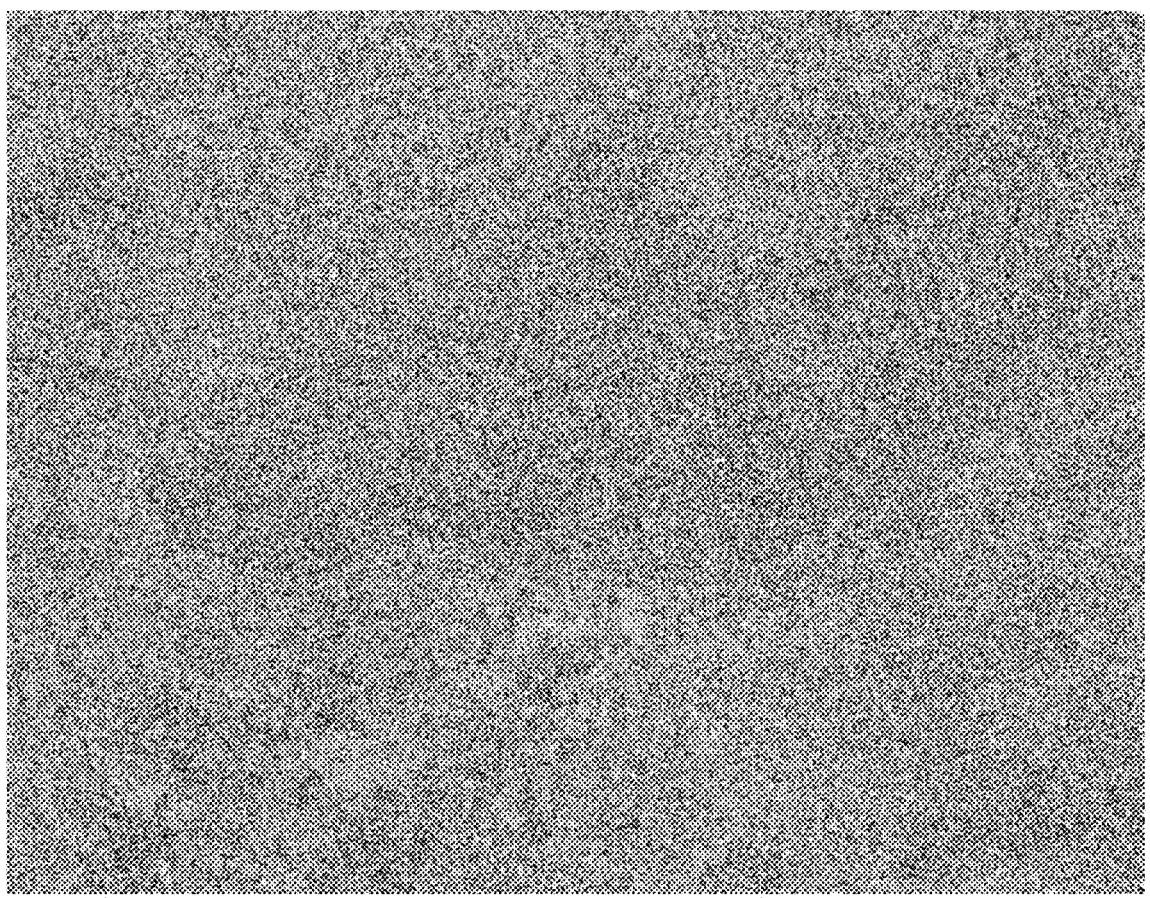
FIG. 4 is the HH polarized scan after filtering electromagnetic noise according to some embodiments of the invention.

An exemplary HH polarized scan (e.g., Bs scan) after filtering electromagnetic noise according to some embodiments of the invention is given in FIG. 4. As one can see in comparison to the scans in FIGS. 3A and 3B, the filtered scan is relatively homogeneous with no large noisy areas or portions. FIGS. 4-7 are gray scale representations of the intensity level at each pixel in the scans. FIGS. 4-7 were created by reconverting the intensity levels used for calculating the various steps of the method from dB to gray scale, using the invert equation of equation (1).

Figure 5:
FIG. 5 is a water composition map according to some embodiments of the invention.

In operation 240, embodiments of the method may include creating a water composition map based on typical salinity values of various (e.g., a set of) types of water sources and the filtered first scan. In some embodiments, typical salinity values of various types of water sources may be stored in a database associated with processor 112, for example, in storage unit 120. Different water sources such as, salty seas, lakes, rivers, swimming pools, sewage pipes and drinking water pipes have different typical reflections recorded and known from the art. This data may be used to create a water composition map that includes all the undesired water sources, for example, the map may include mapping all reflections related to water sources other than drinking water (e.g., in urban areas sources like rivers, swimming pools and sewage pipes). An exemplary process of creating a water composition map is given in equation (6).

$$Ks = aBs^2 + bBs + c \quad (6)$$

wherein: a is the average salinity of drinking water, b is the average salinity of open sweet water sources (e.g., swimming pools, fountains and lakes) and c is the average salinity of sewage water. An exemplary water composition map is given in FIG. 5. FIG. 5 is mostly dark, the dark part is where no water is detected.

In some embodiments, the water salinity may be calculated based on the chemical composition of the water. The amount of chemicals that may be solute in the water may affect the dielectric properties of the water. It is well known in the art that the amount of salinity may change the dielectric constant of the water, the higher the salinity the higher is the dielectric constant, for a given frequency. Underground water having different dielectric constants may have different water different typical microwave reflections at the same conditions. Some exemplary solutes such as chlorine, calcium and bicarbonates may contribute to the salinity of the water. Drinking water at different areas on the globe has different salinity levels, for example, the amount of calcium in the drinking water in Israel is much higher than the amount of calcium in the drinking water in Germany. In Israel the rocks and soil contain large amount of limestone which contributes to the amount of calcium in the water. In some areas there may be a difference in the chemical composition of the water even between two neighboring cities, due to fluorination of the water or other manipulations of the drinking water conducted by, for example, the local municipality.

In some embodiments, when the water composition is calculated for example using equation (6) above, and may include selecting the "a" parameter, "b" parameter and/or the "c" parameter of equation (6) based on the chemical composition of the water in the area. In some embodiments, selecting the "a" parameter may include selecting the parameters from a lookup table stored in a memory associated with processor 112, for example, in storage unit 120. The lookup table may include a list of various "a", "b", and/or "c" parameters for water having various chemical compositions. Additionally or alternatively, selecting "a", "b", parameter and/or "c" parameter may include modifying (e.g., by multiplying with a "salinity parameter") the "a", "b", parameter and/or "c" parameter. The salinity parameter may be stored in a memory associated with processor 112, for example, in storage unit 120.

In operation 250, embodiments of the method may include identifying a first type of water sources using the water composition map and the filtered first scan. Exemplary equations (7) and (8) may be used for calculating value of the first water source.

$$Wc' = Bs \cdot Ks^{Ks} \quad (7)$$

$$Wc = -d \cdot Wc'^2 - e \cdot Wc' - f \quad (8)$$

wherein: Wc is the calculated value of the first water source (e.g., drinking water) in each pixel in the scanned area, d is a constant related to an urban area, e is a constant related to a semi-urban area and f is a constant related to a non-urban area. These constants may vary with the type of water source, the type of soil, the amount of moisture in the soil, precipitations (e.g., rain) in the area in a predetermined time interval prior to the calculation (e.g., a week), or the like.

In some embodiments, Wc may be calculated additionally using a correction parameter based on at least one of: the type of the soil at the area, the density of the soil at the area and a topography of the scanned area. In some embodiments, calculating Wc may include reducing a moisture level from the identified water sources received from a database. The moisture level may be calculated based on at least one of: moisture characteristics of a soil in the area and an amount of precipitations (e.g., rain) in the area in a predetermined time interval prior to the calculation (e.g., a week).

Figure 6:
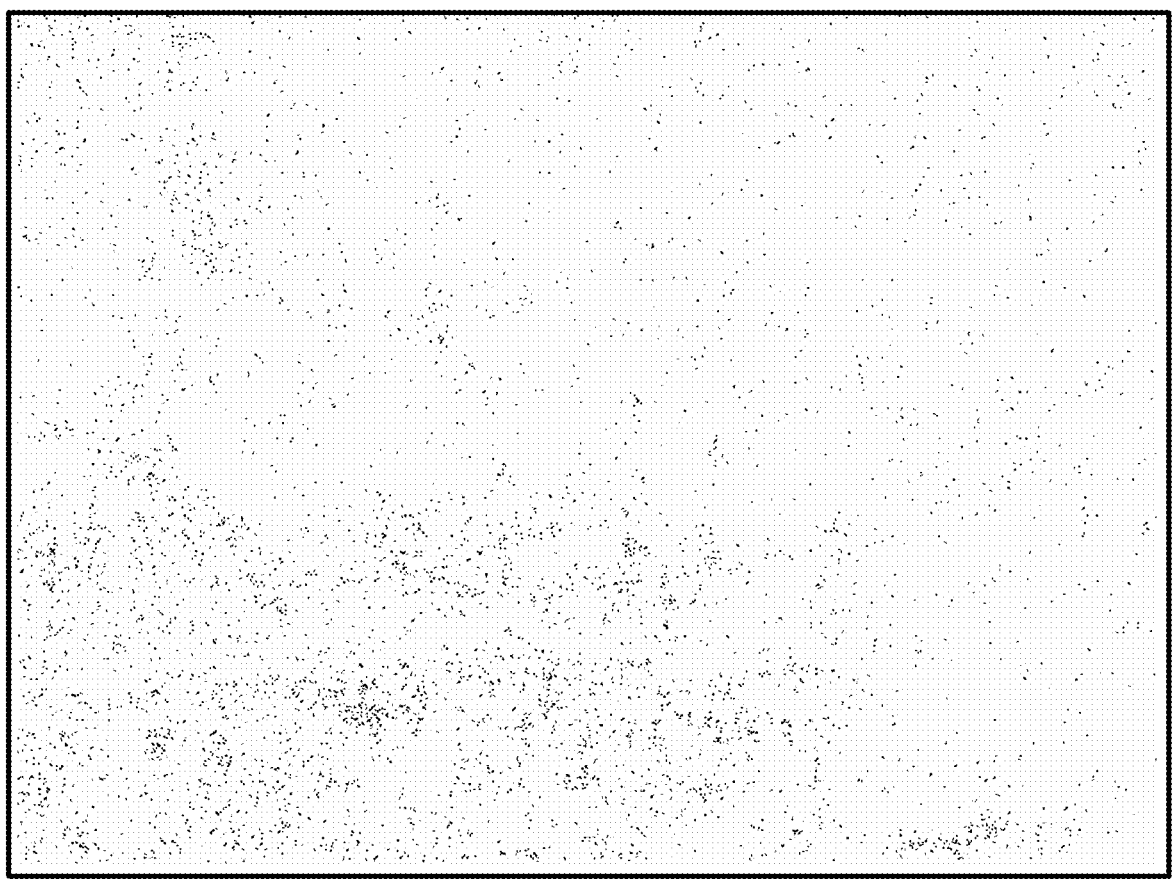
FIG. 6 is a map with identified drinking water sources according to some embodiments of the invention.

FIG. 6 is an exemplary map with identified water sources according to some embodiments of the invention, showing water content in a geographical representation. Since the detection resolution of the drinking water is equal to the resolution of the first, second and optionally third scans, drinking water or other water sources smaller than the scanned resolution (e.g., 3 m$^2$, 6 m$^2$, 12 m$^2$, or the like) cannot be detected.

Figure 7:
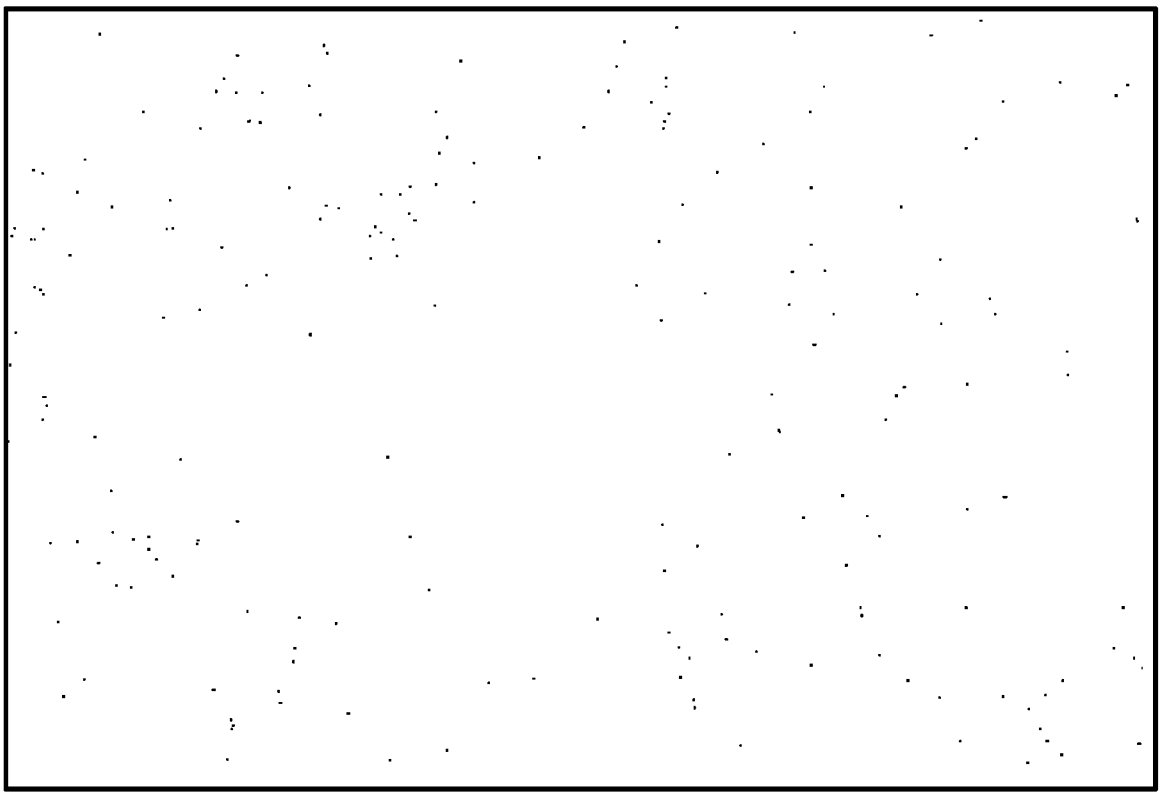
FIG. 7 is a map with identified drinking water leakages according to some embodiments of the invention.

FIG. 7 is an exemplary map with identified drinking water leakages (e.g., a Wc map) according to some embodiments of the invention. Each small dot on the map has different gray scale (e.g., different water content) and corresponds to water leakage. Some water leakages may be larger than areas covered by a single pixel and may include several pixels. Embodiments of the method may include summing or combining together neighboring pixels identified as drinking water leakages to define a single leakage. The intensity levels may be calculated for example in dB values and may be converted to water capacity.

In operation 260, embodiments of the method may include calculating the water content at different locations in the area based on the identified first type of water sources. In some embodiments, since every identified water source (e.g., leakage) has its own intensity value, these values may be used to calculate the water content related to each water source. The higher the intensity level (e.g., the higher the Wc at that pixel or the sum of Wc in neighboring pixels) the higher is the water content. Embodiments of the method may include converting the calculated water content from reflection intensity levels to quantities of water capacity for the different area location, for example, in gallons per hour, cubes per hour, etc. The water capacity may be proportional to the intensity. Different constants may be used to convert the intensity levels to capacities as a function of the capacity unit used (e.g., gallons/hour, cubes/hour, etc.) The calculated intensity level for each pixel may be multiplied by a known constant (e.g., different constants may be used for different capacity units) converting the intensity levels into water capacities. Some embodiments may include summing capacities calculated for neighboring pixels. Water capacities calculated for several neighboring pixels, each corresponding to a location in the scanned area, may indicate that a large underground water leakage may be found in the corresponding locations.

Figure 8:
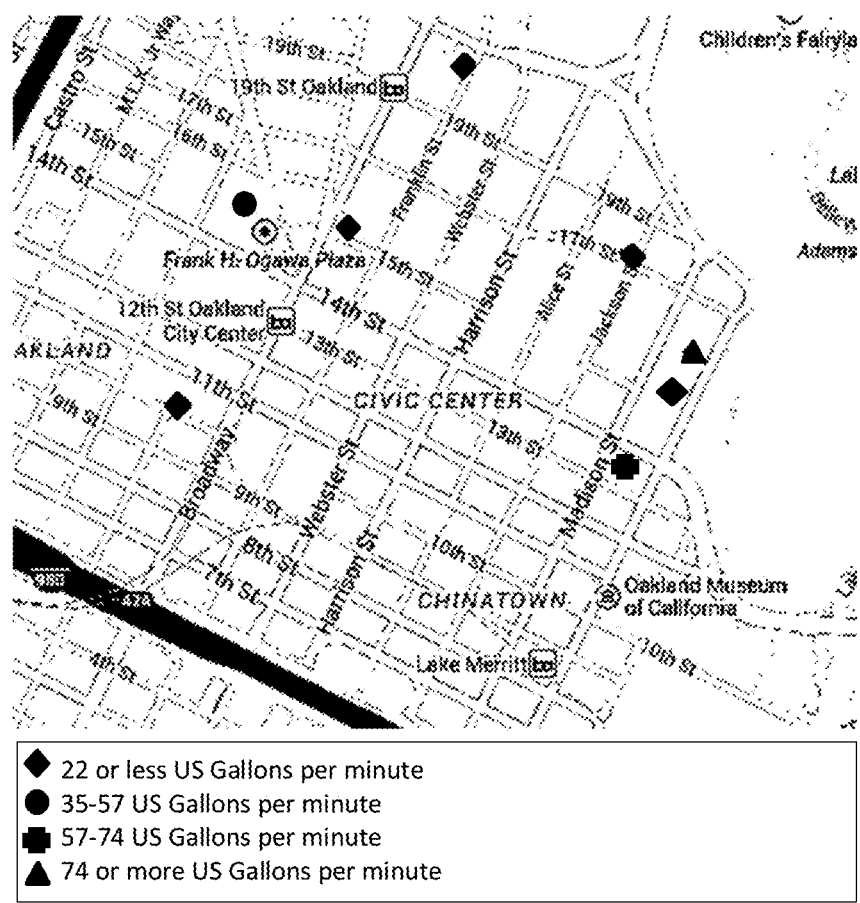
FIG. 8 is a graphical map showing the amount and location of water leakages according to some embodiment of the invention.

Embodiments of the method may include displaying the converted quantities of water capacity on a graphical map of the one or more scanned area. The converted quantities may be displayed on: a street map of an urban area, a road map of a county, satellite map, or the like. The converted quantities of water capacity may be displayed on screen 132 included in user interface 130. An exemplary street map of the Oakland, Calif. city center with locations of drinking water leakages is shown in FIG. 8. Since the received scans may include information (e.g., pixels) from a relatively large area, the geographical map presenting the data to a user (e.g., city official) may include only a portion of the scanned area. The user may shift the geographical map on the screen (e.g., using a mouse or a keyboard) covering all areas of interest (e.g., the city quarters) in the scanned area. Some of the detected leakages, illustrated as small gray dots in FIG. 7 were given a water capacity value and location in the corresponding geographical map (e.g., using coordinates). For example, as illustrated in FIG. 8 each of the marks located in a particular place on the map presents different amounts of water leakage (e.g. in gallons/hour). It should be appreciated by those skilled in the art that the displayed information may be displayed on top of a Geographic Information System (GIS). It should be further appreciated that additional information may be displayed alongside the water capacity value and location information, such as, water pipes, water valves and the like. Such a representation may allow better understanding of the source of a water leakage and may facilitate decision making in real time.

Figure 9:
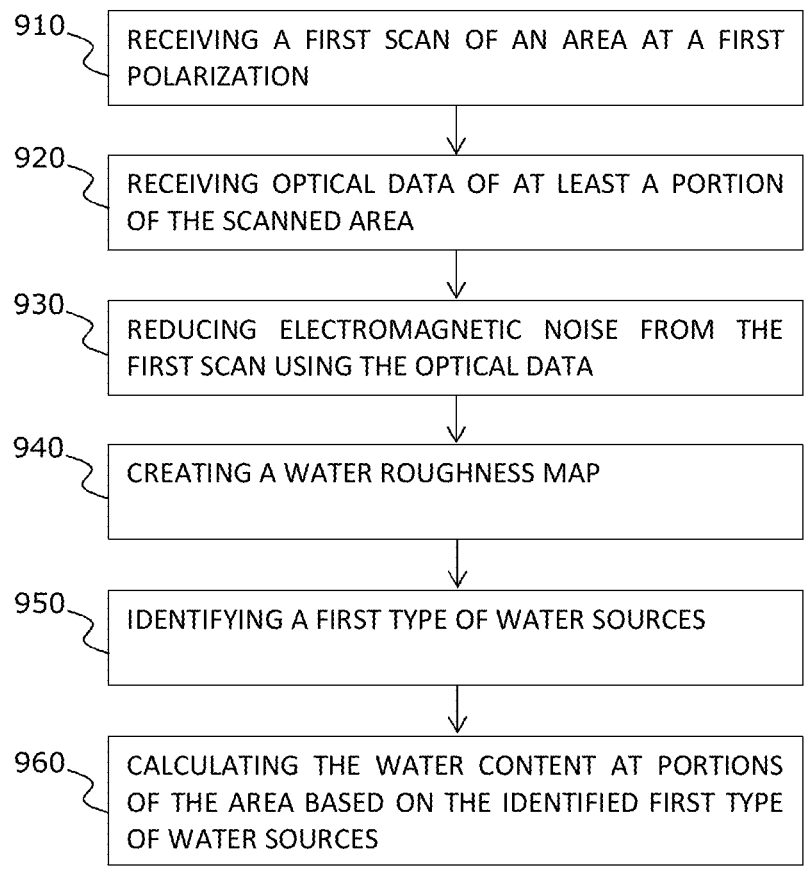
FIG. 9 is a flowchart of a method of detecting underground water according to some embodiments of the invention.

Reference is made to FIG. 9, a flowchart of an exemplary method of remote detecting of underground water according to some embodiments of the invention. Embodiments of the method may be performed, for example, by system 100 or by another system. In operation 910, embodiments of the method may include receiving a first scan of an area at a first polarization. Operation 910 may be substantially the same as operation 210 of the method illustrated in FIG. 2 and may include the operations, steps and equations described above with respect to operation 210.

In operation 920, embodiments of the method may include receiving optical data representing at least a portion of the scanned area. The optical data may be captured in a wavelength in the range of 1 millimeter to 10 nanometers (e.g., from the infrared to the ultraviolet spectrum). The optical data may be received from at least one capturing device or a sensor (such as sensor 150 or 152) located either on platform 155 or elsewhere. The capturing device may include an infrared (IR) camera, a visible light camera and/or an ultraviolet (UV) camera. The optical data may include a satellite optical image, an aerial photograph or the like. Exemplary optical data may include an IR image of the area captured by an IR camera, a visible light photograph of the area (e.g., an aerial photograph) or a UV scan of the area.

In operation 930, embodiments of the method may include filtering electromagnetic noise from the first scan using the optical data. In some embodiments, the method may include comparing the color (e.g., the wavelength) or intensity of neighboring pixels in the optical data to detect differentiations or unexpected colors in the optical data. For example, IR radiation may vary due to temperature differences at various locations in the scanned area. Underground water may cool down the temperature of the soil and land being wetted by the underground water leakage, in comparison to nearby soil and land. In some embodiments, a detection of an area cooler than nearby areas may indicate the presence of underground water. In yet another example, the presence of underground water may affect the presence of vegetation at certain areas and/or the color of the vegetation or soil. For example, the presence of underground water: may cause growth of significant lichen in between paving-stones in a flagging, may cause regeneration of green leaves in some of the vegetation in substantially dry vegetation (e.g., during the summer), may cause a change in the color of the soil (e.g., to become darker) or the like. These changes in the color, if detected, may indicate the presence of unground water. In some embodiments, the detected indication to a presence of underground water may be used to filter the EM noise from the first scan.

Some embodiments may include receiving a second scan of the area at a second polarization, the second scan including second L band microwave reflections from the area, the second scan being from the first sensor as discussed with respect to operation 220 of the embodiment illustrated in FIG. 2. In some embodiments, filtering the EM noise from the first scan may further include using the second scan, as discussed with respect to operation 230 of the embodiments of FIG. 2.

Operations 940-960 may be substantially the same as operations 240-260 of the embodiments of FIG. 2 and may include the steps, operations and equations of operations 240-260. The embodiment of FIG. 9 may include any operation or step that may be included and disclosed with respect to the embodiment of FIG. 2.

Figure 10:
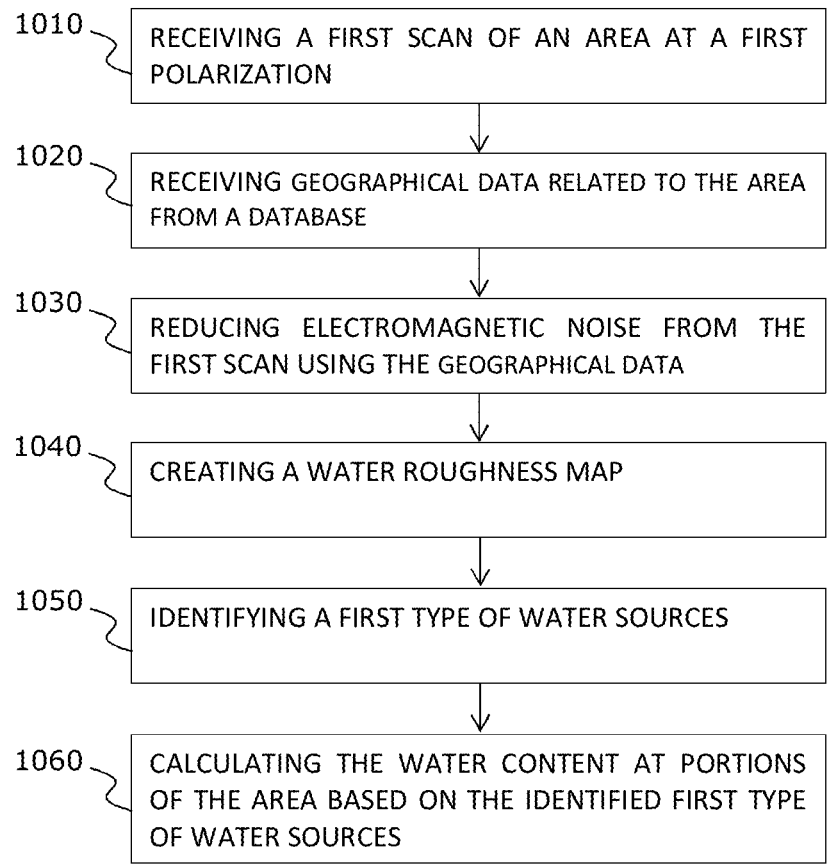
FIG. 10 is a flowchart of a method of detecting underground water according to some embodiments of the invention.

Reference is made to FIG. 10, a flowchart of an exemplary method of remote detecting underground water according to some embodiments of the invention. Embodiments of the method of FIG. 10 may be performed for example by system 100 or by another system. In operation 1010, embodiments may include receiving a first scan of an area at a first polarization. Operation 1010 may be substantially the same as operation 210 of the embodiments of FIG. 2 and may include the operations, steps and equations disclosed above with respect to operation 210.

Figure 11:
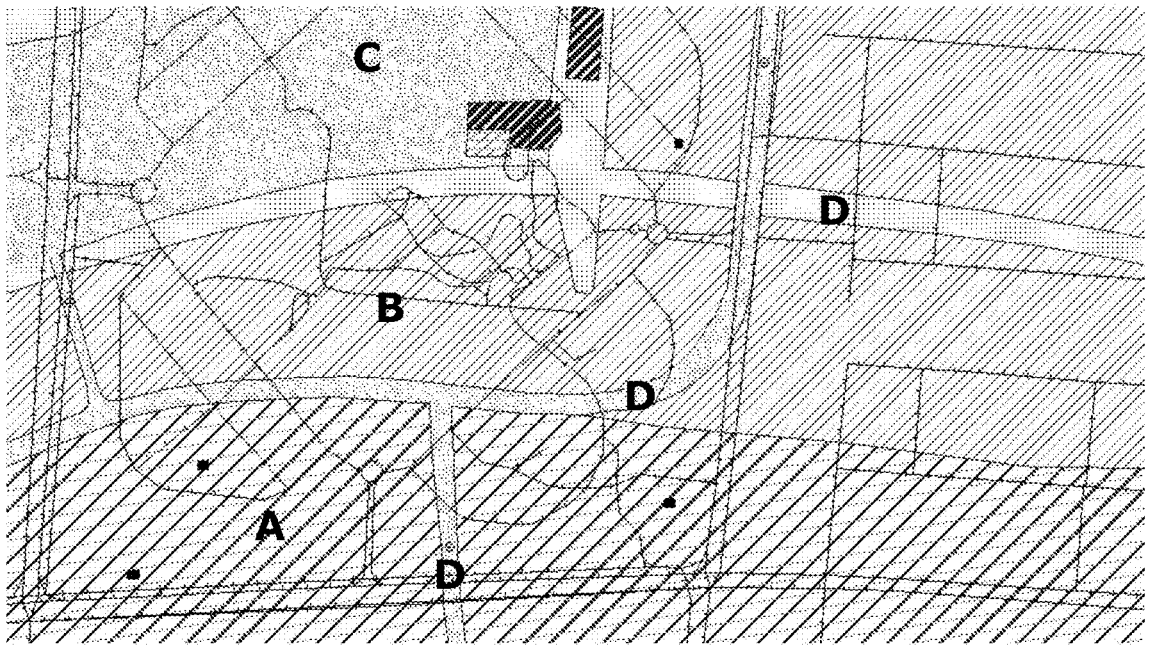
FIG. 11 is an example for graphical representation of geographical data according to some embodiments of the invention.

In operation 1020, embodiments may include receiving geographical data related to the area from a database. In some embodiments, the geographical data may include a land cover data related to the area. Exemplary land cover may include types such as: a dense urban area, an urban area, a park, an agricultural area, an industrial area, a village and/or paved area. In some embodiments, the land cover data may include classification of various portions in the scanned area into various land cover types, for example, the land cover types listed above. A graphical representation of a scanned area classified to various land cover types is illustrated in FIG. 11. FIG. 11 is a map of a portion of an area presenting 4 land cover types at different location on the map according to one embodiment. The land coves: at location A may be classified as an industrial area, at location B may be classified as urban area, at location C may be classified as a park and at locations D may be classified as paved areas. Other classifications may be used.

In some embodiments, the geographical data may include a location, length, width and height of objects (e.g., buildings) in the scanned area. For at least some of the buildings in the area the location and dimensions of each building may be included in the geographical data.

In operation 1030, embodiments may include filtering electromagnetic noise from the first scan using the geographical data. In some embodiments, filtering the electromagnetic noise may include assigning filtering parameters to each portion of the area based on the land cover type of the classification of the portions of the area. The filtering parameters may be related to the amount of scattering of the microwaves that is typical for each land cover type.

Figure 12:
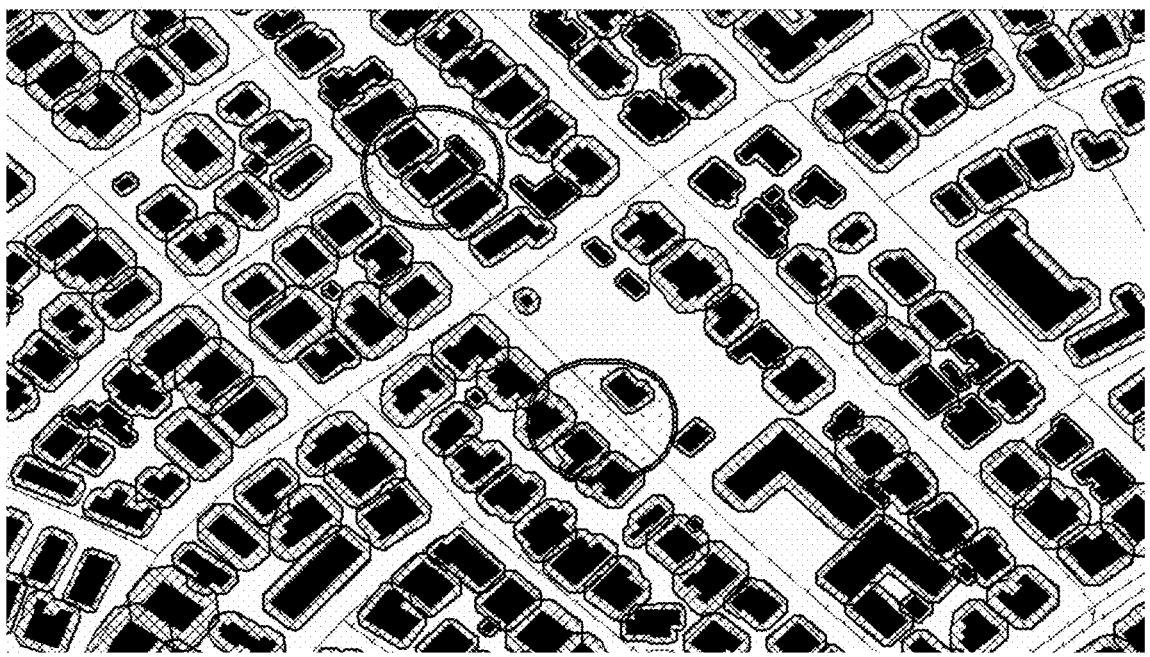
FIG. 12 is an example for graphical representation of geographical data according to some embodiments of the invention.

In some embodiments, filtering the electromagnetic noise may include calculating the size and location of blind spots areas in proximity to objects in the area, wherein the objects block microwave reflection from the blind spots areas from reaching the sensor. An exemplary calculation of blind spot areas near a building may be done using for example equation (9).

$$S = \tan \alpha \times Hbl \tag{9}$$

Wherein S is the size (in m$^2$) of the blind spot area, $\alpha$ is the off-nadir angle from the satellite to the ground and Hbl is the height of the building. A calculation done for 3 stores building resulted in a blind spot area of 4 m$^2$. FIG. 12 is an illustration of calculated blind spot areas created by nearby buildings according to one embodiment. The squared patterned areas around the dark objects are the blind spot areas. These blind spot areas may be used to filter false readings, for example, if an indication is made that there is a leakage of water under an area located in the blind spot area (illustrated as a circle), embodiments may include concluding that these indications are false readings and should be neglected.

Some embodiments may include receiving a second scan of the area at a second polarization, the second scan including second L band microwave reflections from the area, the second scan being from the first sensor as discussed with respect to operation 220 of FIG. 2. In some embodiments, filtering the EM noise from the first scan may further include using the second scan, as discussed with respect to operation 230 of FIG. 2.

Operations 1040-1060 may be substantially the same as operations 240-260 of FIG. 2 and may include the steps, operations and equations of operations 240-260. The embodiment of FIG. 10 may include any operation or step that may be included and disclosed with respect to the embodiments of FIG. 2 and/or FIG. 9.

Figure 13:
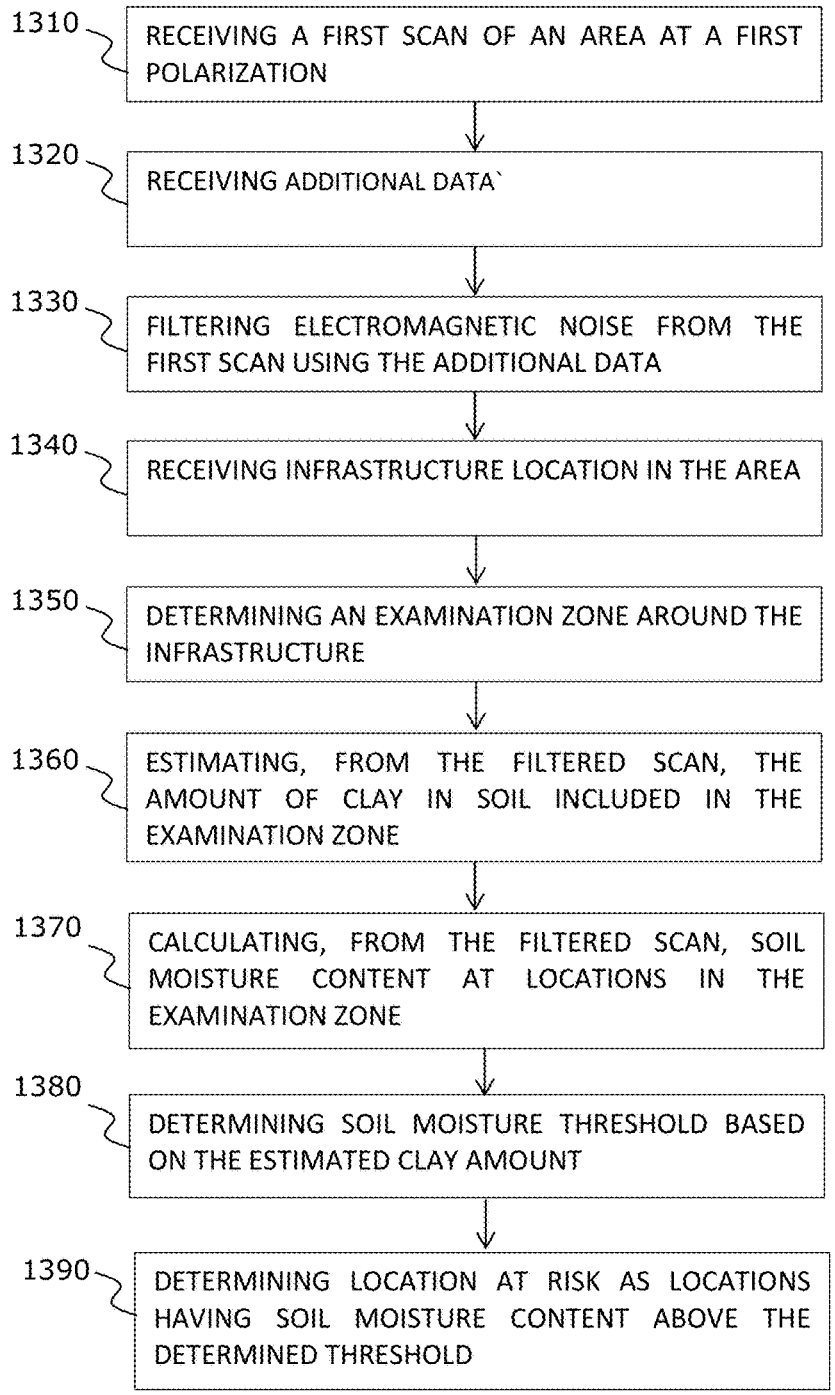
FIG. 13 is a flowchart of a method of determining infrastructure risk zones in infrastructures and/or land according to some embodiments of the invention.

Reference is now made to FIG. 13 which is a flowchart of a method of determining infrastructure risk zones according to some embodiments of the invention. The method of FIG. 13 may be performed, for example, by system 100 or by another system. In operation 1310, a first scan of an area at a first polarization may be received from an RF radiation sensor. In some embodiments, the first scan may include first RF reflections from the area at a first resolution, the sensor being located at least 50 meters above the area. In some embodiments, the area may at least partially include the infrastructure, for example, road 1450 illustrated in FIG. 14. In some embodiments, the area to be scanned may be selected to include at least one portion of an infrastructure of interest, for example, a portion of a highway, a portion of an industrial area, an entire shopping center and the like.

In some embodiments, operation 1310 may be substantially the same as operations 210, 910 and 1010 of the methods of FIGS. 2, 9 and 10 respectively. In operation 1320, additional data may be received. For example, the additional data may include receiving a second scan of the area at a second polarization, as discussed in detail with respect to step 220 of the method of FIG. 2. In some embodiments, the additional data may further include receiving a third and fourth scans from the area, as discussed in detail with respect to step 220 of the method of FIG. 2.

In another example, the additional data may include optical data representing at least a portion of the scanned area, as discussed in detail with respect to step 920 of the method of FIG. 9. In yet another example, the additional data may include geographical data related to the area, received from a database, as discussed in detail with respect to step 1020 of the method of FIG. 10.

In operation 1330, electromagnetic noise may be filtered from the first scan using the additional data. For example, the electromagnetic noise may be filtered according to operations 230, 930 and/or 1030 of the corresponding methods of FIGS. 2, 9 and 10.

In operation 1340, infrastructure location in the area may be received, for example, from a database associated with system 100 (e.g., storage unit 120), over the internet from an external database and the like or may be obtained by a sensor located at least 50 meters above the examined area such as an aerial photo of the area. For example, the location may be included in a map depicting roads, rails, gas stations and the like. In some embodiments, the first scan may be selected to cover the area at which at least a portion of the infrastructure is located (e.g., a portion of a road, a portion of a rail, and the like). Examples of such areas are illustrated in FIGS. 14-17 including infrastructure facilities or systems (e.g., roads) 1450, 1550, 1555, 160 and 170.

Figure 16:
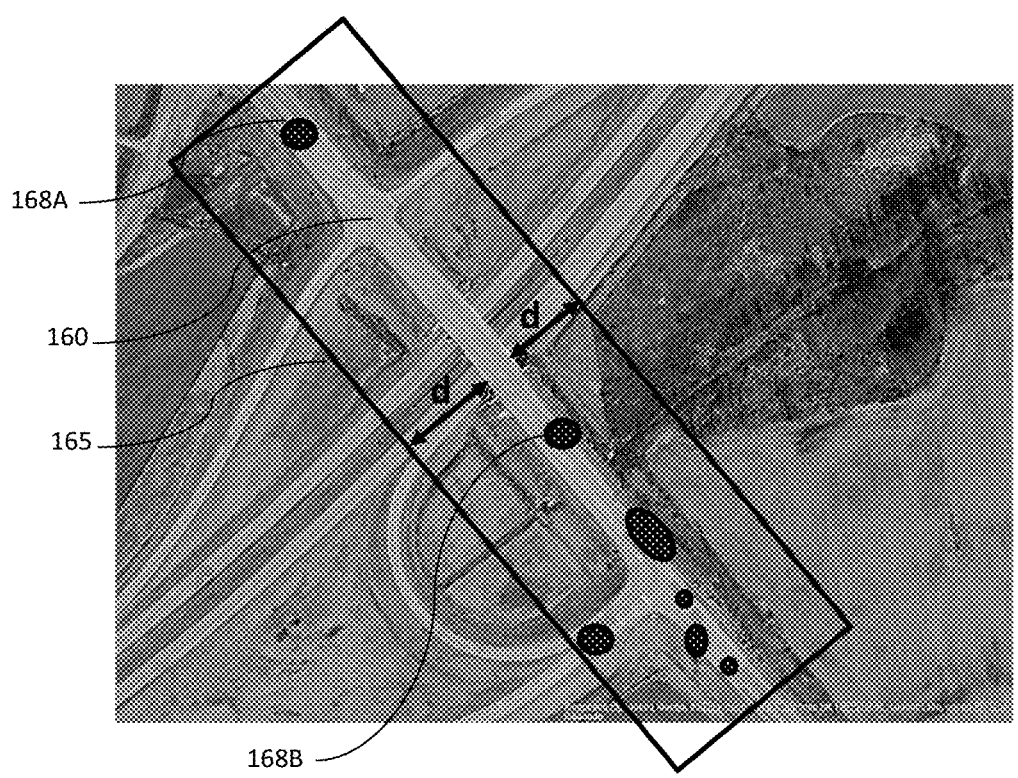
FIG. 16 is an example of graphical representation of infrastructure risk zones due to high soil moisture content according to some embodiments of the invention.

In operation 1350, an examination zone may be determined around the infrastructure. In some embodiments, the examination zone may be determined as the area between two or more boundaries located at constant distances from the infrastructure. For example, a constant distance 'd' (e.g., 20 meters) may be determined from each side of road 160, as illustrated in FIG. 16, defining an examination zone 165.

In some embodiments, the method may further include receiving topographical data (e.g., a topographical map) of the area, for example, from a database associated with system 100 (e.g., storage unit 120), over the internet from an external database, a digital elevation map and the like. For example, a topographical map with a portion of infrastructure 1450 (in this case, a road) is given in FIG. 14. In some embodiments, a drainage divide surrounding at least part of the infrastructure may be identified (e.g., the borders of a basin surrounding the infrastructure). As used herein a "drainage divide" (also known in the art as water divide, divide, ridgeline, watershed, water parting or height of land) is elevated terrain that separates neighboring drainage basins. Alternatively, on a rugged land, the divide lies along topographical ridges, and may be in the form of a single range of hills or mountains, known as a dividing range.

Figure 14:
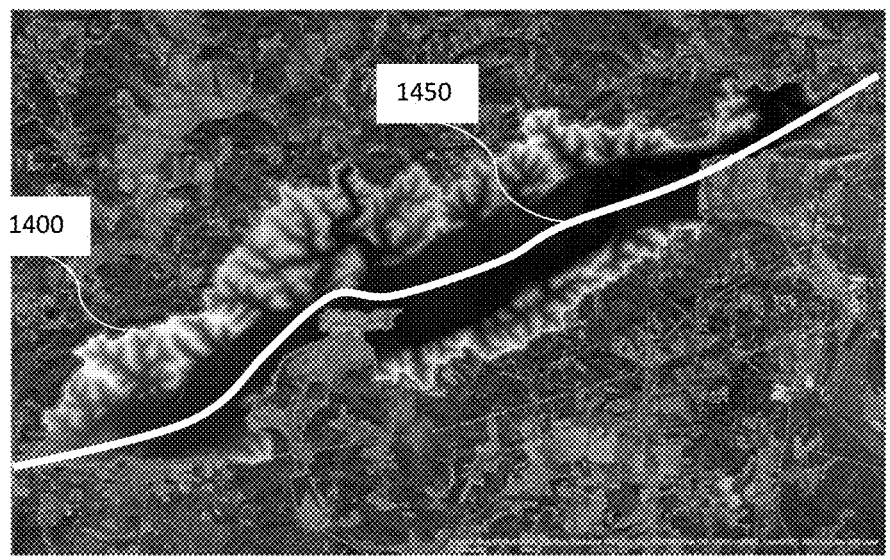
FIG. 14 is an example of graphical representation of a drainage divide in a topography, according to some embodiment of the invention.
Figure 15:
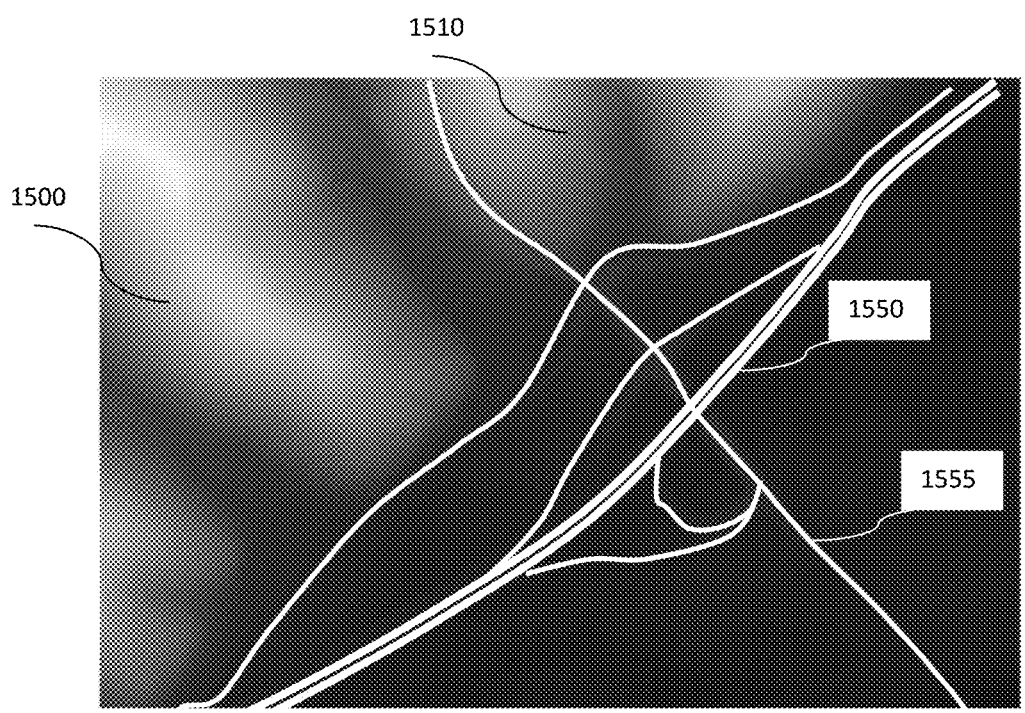
FIG. 15 is an example of slopes mapping around an infrastructure according to some embodiments of the invention.

For example, drainage divide 1400 surrounding road 1450 may be identified in the area of FIG. 14. In order to identify the drainage divide, the slopes in the area may be mapped. FIG. 15 is an illustration of mapped slopes 1500 and 1510 near roads 1550 and 1555. In some embodiments, the examination zone may be the drainage divide.

In some embodiments, the examination zone may be dynamically determined based on real time information related to changes in a determined basin size around the infrastructure, as discussed with respect to equation 11 hereinbelow. The slopes (e.g., location and/or grade) may be a dynamic value that may change according to the soil parameters. For example, strength of a rock mass may depend on the type of rock and the presence and nature of discontinuities such as joints or other fractures. The more discontinuities present in bedrock, the greater the likelihood of rock instability. Rock type may affect land sliding due to the differences in the strength of surface material between two different types of rocks. For example, soils derived from schists or shales may contain high percentages of clay. These soils may have lower strength characteristics than coarser-grained soils such as those derived from granitic bedrock. Therefore, soils that contain more clay may require determining a wider examination zone than would be required for sandy soils.

In operation 1360, an amount of clay in soil included in the examination zone may be estimated from the filtered first scan. For example, filtered RF reflections (Bs) associated with locations (coordinates) inside the examination zone may be used for estimating the amount of clay in soil, using for example, equation 10.

$$\text{Clay \%} = 4.35 * \frac{Bs}{1.81} \tag{10}$$

In some embodiments, the amount of clay in the soil (which may be expressed as a percentage) may affect the ability of the soil to absorb water without swelling and/or shrinkage. In some embodiments, the higher the clay percentage, the greater the swelling and/or shrinkage capacity of the wet soil. In some embodiments, the amount of clay may affect the examination zone, for example, when combined with a location of a slope. In some embodiments, for each slope (defined as a change in the height of land higher than a threshold grade) a grade may be calculated based on the area of the examination zone (e.g., basin size) in $Km^2$ divided by the quotient of the percentage of clay at the landslide area and the average slope percent (slope percent=(amount of rise/amount of run)×100).

$$Grade = \frac{Basin\ size\ (from\ the\ infrastrucre\ to\ the\ drainage\ divide)}{\left(\frac{clay\ \%}{slope\ \%}\right)} \quad (11)$$

Equation 11 may allow the examination zone (e.g., the basin size) to be determined according to a required soil/land stability defined by a required grade. In some embodiments, the size of the examination zone area (e.g., in $Km^2$) may be determined such that for a given clay amount and a given average slope the calculated grade may be higher than a predetermined grade.

In operation 1370, soil moisture content at locations in the examination zone may be calculated from the filtered first scan. The soil moisture content may be calculated using any method known in the art. In some embodiments, soil moisture content may be calculated using the methods disclosed in operations 240-260 of FIG. 2.

In operation 1380, a soil moisture threshold may be determined. For example, the threshold may include soil moisture content above 30% (determined by gravimetric analysis). In some embodiments, the threshold may be determined based on the estimated clay amount. For example, for each estimated amount of clay, a corresponding predetermined threshold value of soil moisture content may be determined (e.g., using a look up table based on experimental data and/or simulated data). In some embodiments, a correlation between the amount of clay (which may be expressed as a percentage) and the distance 'd' of the boundaries of the examination zone from the infrastructure may be a linear correlation or any other polynomial correlation. In some embodiments, the calculated linear correlation may be a starting point for forming the lookup table, which may be updated and refined using new collected experimental and/or actual data.

In some embodiments, the predetermined soil moisture content threshold may be dependent on both the slope and the chemical composition of the soil, as given in equation 12.

$$SMT = \left|avgNonClay\% * \frac{1}{\tan*slope\ \%}\right| \quad (12)$$

Where, SMT is the soil moisture threshold, NonClay % is the average amount in % of other materials in the soil, and slope percent.

In Operation 1390, at least one location at risk may be determined as having soil moisture content above the determined threshold.

In some embodiments, the at least one location at risk may be displayed (e.g., graphically) to a user. Examples of such presentations are given in FIGS. 16 and 17. FIG. 16 is a map showing locations at risk 168A and 168B in examination zone 165 near road 160. As shown in FIG. 16, the landscape over which road 160 is running is substantially flat, therefore, examination zone 165 may be determined using constant distances 'd' from the two sides of road 160.

Figure 17:
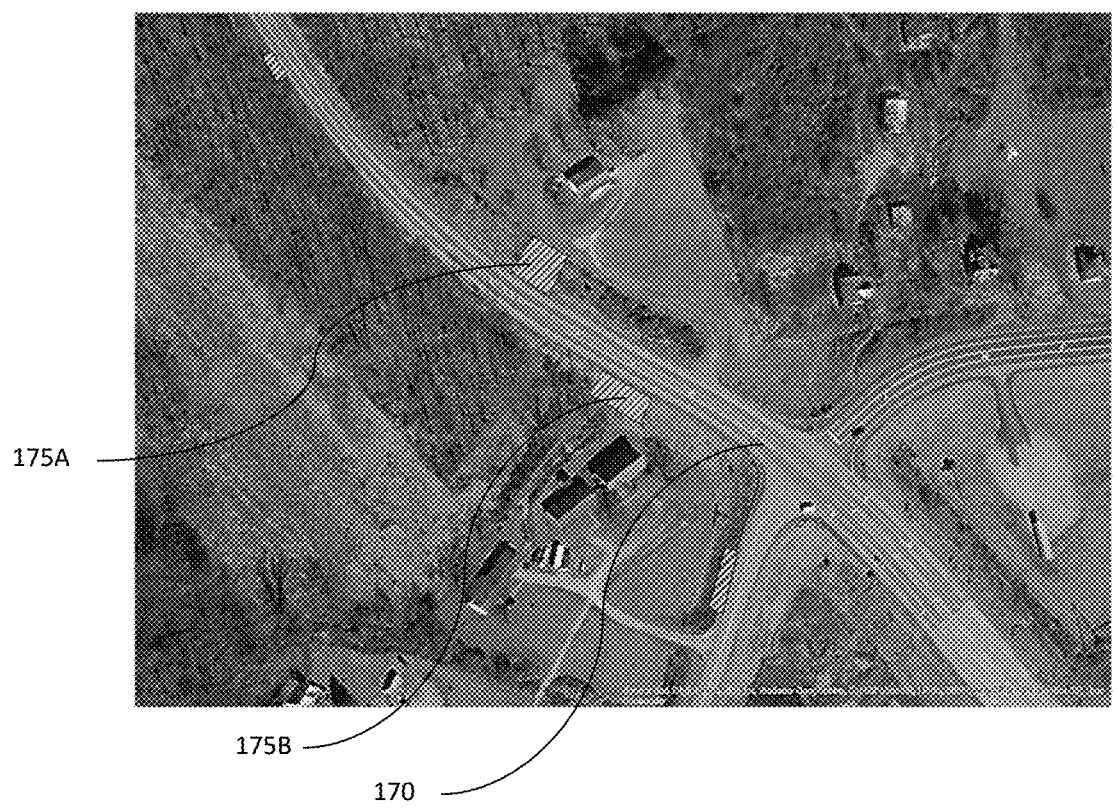
FIG. 17 is an example of graphical representation of infrastructure risk zones due to land collapse (landslide) according to some embodiments of the invention.

FIG. 17 is a map showing locations at risk 175A and 175B near road 170 running along a basin(and thus potentially subjected to the influence of slopes). Accordingly, a drainage divide may be used as the examination zone for identifying locations at risk 175A and 175B.

Other properties of water, such as the chemistry of the water, may further affect buildings and infrastructure. For example, an amount of salt in the water (e.g., the salinity level) may further affect the harmful nature of the water with respect to materials/building included in the infrastructure. For example, high salinity levels may cause rapid corrosion in steel reinforcing bars included in a reinforced concrete. Accordingly, determining the type of water in the soil, using for example, the methods disclosed in operations 240 and 250 of the method of FIG. 2 may allow to further estimate the risk of corrosion in the infrastructure.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of determining infrastructure risk zones by at least one processor, the method comprising:
   receiving, from a radiofrequency radiation sensor, a first scan of an area at a first polarization, the first scan including first radiofrequency reflections from the area at a first resolution, the sensor being located at least 50 meters above the area, wherein the area at least partially comprises infrastructure;
   receiving additional data;
   filtering electromagnetic noise from the first scan using the additional data;
   estimating an amount of clay in soil in the area, from the filtered first scan;
   receiving infrastructure location in the area;
   determining an examination zone around the infrastructure, based on the infrastructure location and the estimated clay amount;
   calculating soil moisture content at locations in the examination zone, from the filtered first scan; and
   determining at least one infrastructure risk zone as a location in the examination zone having soil moisture content above a predetermined threshold, wherein the threshold is determined based on the estimated clay amount.

2. The method of claim 1, further comprising:
   receiving topographical data of the area;
   identifying a drainage divide surrounding at least part of the infrastructure,
   wherein the examination zone is the drainage divide.

3. The method of claim 1, wherein the additional data comprises at least a second scan of the area at a second polarization, the second scan including second radiofrequency reflections from the area at a second resolution, the second scan being from the radiofrequency radiation sensor used to obtain the first scan.

4. The method of claim 1, further comprising converting the first and second radiofrequency reflections from grey scale levels to intensity levels.

5. The method of claim 3, wherein the first polarization is a horizontal polarization, and the second polarization is a vertical polarization.

6. The method of claim 3, further comprising:
receiving a third scan of the area at the second polarization, the third scan including third reflections from the area at a higher resolution than the first and second scans; and
receiving a fourth scan of the area at a third polarization, the fourth scan including fourth reflections from the area,
the fourth and thirds scans being from the radiofrequency radiation sensor used to obtain the first scan,
wherein, filtering electromagnetic noise from the first scan comprises using the third and fourth scans to filter the noise.

7. The method of claim 1, wherein filtering electromagnetic noise comprises at least one of:
filtering electromagnetic reflection noise received from solid objects located in the scanned area; and
filtering electromagnetic bouncing reflection noise from solid objects located in the scanned area.

8. The method of claim 1, wherein the additional data comprises optical data of at least a portion of the scanned area, and wherein identifying the first type of water comprises analyzing the optical data to detect changes in colors in portions of the area.

9. The method of claim 1, wherein the additional data comprises geographical data related to the area received from a database and wherein the geographical data comprises land cover data related to the area.

10. The method of claim 9, wherein the land cover-data related to the area comprises classification of portions of the area into various land cover types, and wherein filtering the electromagnetic noise comprises assigning filtering parameters to each portion of the area based on the classification of the portions of the area to the cover type.

11. The method of claim 9, wherein the geographical data comprises a location, and dimensions of buildings in the area, wherein filtering the electromagnetic noise comprises calculating the size and location of blind spots areas in proximity to objects in the area, and wherein the objects block radiofrequency reflection from the blind spots areas from reaching the sensor.

12. A system for determining infrastructure risk zones, the system comprising:
a processor; and
a non-transitory computer readable medium having stored thereon computer-executable instructions which when executed by the processor cause the processor to:
receive, from a radiofrequency radiation sensor, a first scan of an area at a first polarization, the first scan including first radiofrequency reflections from the area, the sensor being attached to an object located at least 50 meters above the area;
receive additional data;
filter electromagnetic noise from the first scan using the at least one additional data;
estimate an amount of clay in soil in the area, from the filtered first scan;
receive infrastructure location in the area;
determine an examination zone around the infrastructure, based on the infrastructure location and the estimated clay amount;
calculate soil moisture content at locations in the examination zone, from the filtered first scan; and
determine at least one infrastructure risk zone as a location in the examination zone having soil moisture content above a predetermined threshold, wherein the threshold is determined based on the estimated clay amount.

13. The system of claim 12, wherein the processor is further configured to: receive topographical data of the area; and
identify a drainage divide surrounding at least part of the infrastructure, and wherein the examination zone is the drainage divide.

* * * * *